United States Patent [19]

Zuk et al.

[11] Patent Number: 5,800,175
[45] Date of Patent: Sep. 1, 1998

[54] METHOD AND APPARATUS FOR RE-IMPLANTING TEETH

[76] Inventors: Zenon Zuk, 201 Calle Miramar #11, Redondo Beach, Calif. 90277; Lubomyr T. Romankiw, #7 Dunn La., Briar Cliff Manor, N.Y. 10510; Roger Stambaugh, 1245 16th St., Suite 206, Santa Monica, Calif. 90404

[21] Appl. No.: 615,849

[22] Filed: Mar. 12, 1996

[51] Int. Cl.$^6$ ........................................ A61C 5/00
[52] U.S. Cl. .................. 433/217.1; 433/175; 433/215; 427/2.26; 427/2.1; 118/726
[58] Field of Search ...................... 433/175, 215, 433/217.1; 118/726; 427/2.1, 2.26, 2.29

[56] References Cited

U.S. PATENT DOCUMENTS

| | | | |
|---|---|---|---|
| 2,711,021 | 6/1955 | Parker | 433/175 |
| 4,009,680 | 3/1977 | Fengler | 118/641 |
| 4,126,924 | 11/1978 | Atkins et al. | 427/2.26 |
| 4,247,575 | 1/1981 | O'Connell et al. | 433/217.1 |
| 4,656,083 | 4/1987 | Hoffman et al. | 427/2.29 |
| 4,689,014 | 8/1987 | Krasner | 433/215 |
| 5,004,422 | 4/1991 | Propper | 433/175 |
| 5,380,547 | 1/1995 | Higgins | 427/2.26 |
| 5,534,314 | 7/1996 | Wadley et al. | 118/726 |

*Primary Examiner*—John J. Wilson
*Attorney, Agent, or Firm*—Burns, Doane, Swecker & Mathis LLP

[57] ABSTRACT

A method and apparatus for extraction and re-implantation of a natural tooth, such tooth being cleaned and repaired while extracted. The crown of the repaired tooth is mechanically masked and the tooth is then mounted in a partitioned vacuum cavity wherein gradual application of vacuum is used to degas and dehydrate the tooth root. Following degassing and dehydration of the tooth root a mass of titanium is heated in the cavity partition, by way of an electron beam source, the energy output of the beam source being thereafter ramped up to vaporize the mass. The partition in the cavity is then opened to expose the root to the titanium vapor after which the tooth may be reinserted into the original void.

8 Claims, 2 Drawing Sheets

FIG.—1

METHOD AND APPARATUS FOR RE-IMPLANTING TEETH

BACKGROUND OF THE INVENTION

1. Field of the Invention

The present invention relates to a method and apparatus for re-implanting teeth, and more particularly to a method and apparatus for vapor deposition of titanium onto dental roots to promote their re-implantation through molecular fusion to bone and other tooth supporting structures.

2. Description of the Prior Art

For some time the loss of a tooth has been an event of some finality, resolved mainly by a prosthesis, bridge work, or the like. More recently the complex structure of a bridge has been abandoned in favor of implants. Typically such implants take the form of endosseous posts or inserts fixed, by screwing a metal post, preferably one made of titanium, into the bone with the post structure then extending through the gum. A crown or cover simulating a tooth is then attached to the exposed segment of the post.

Thus the implant post is the principal structure resolving the concerns of mechanical attachments and biological compatibility with the surrounding tissue. In consequence extensive investigative efforts have been directed at dental post implants, their material selection, and their mechanical shape. Examples of such investigations are reported in *Dental Implants, An Alternative to Dentures*, by Richard Seberg, DDS; *Clinical procedure for Single Tooth Abutment*, Council on Dental Materials, Instruments and Equipment, American Dental Association. Included in such investigations were materials like titanium which has been reported in *The In-Vitro effect of a Titanium Implant on Oral Microflora: Comparison with Other Metallic Compounds*, by R. I. Foshi and A. Eley, J. Med. Microbiology—Vol. 27 (1988) 105–107, the Pathological Society of Great Britain & Ireland. See also *Tissue-integrated Prostheses: Osseointegration Research in Toronto*, by G. A. Zarb, A. Schmitt and G. Baker, The International Journal of Periodontics and Restorative Dentistry, 1/1987 and Single Tooth Implant by G. Petri, S. Lewis, J Beumer III, S. Avera and G. Numokawa, CDA Journal Vol 17, No 3 March 1989.

In the foregoing literature the concept of osseointegration to titanium prosthetic implants (posts) is well established. This literature demonstrates that molecular fusion occurs between the titanium oxide on the implanted post and the adjacent bone and other tooth supporting structures.

Nonetheless, the insertion of a post requires invasive and technically demanding drilling of the subjacent bone, with a joint line including interfacing materials of widely differing mechanical properties. Thus, while suitable for the purposes intended, these mechanical aspects may lead occasionally to fracture and failure, a development of concern in the implant technology.

For these reasons a technique which obtains the structural benefits and matching compliance of the original, natural, root is desired and it is one such technique that is disclosed herein.

SUMMARY OF THE INVENTION

Accordingly it is the general purpose and objective of the present invention to provide a method and apparatus useful in reimplanting natural teeth onto the subjacent bone structure.

Other objects of the invention are to provide a process for metal coating of the root of a natural tooth to promote its re-integration once implanted.

Yet further objects of the invention are to provide a vapor deposited coating onto the root of a natural tooth to promote its integration once reinserted.

Briefly, these and other objects are accomplished within the present invention by a novel process in which the extracted tooth root is first cleaned, vacuum dried (dehydrated), and thereafter vapor deposited with titanium. Preferably such vapor deposition is made in a substantial vacuum of 4 to 5 torr or lower with the tooth root first exposed to the vacuum to promote outgassing and dehydration. This initial step is carried out slowly so as not to cause cracks in the outer layers of the root. More precisely, the initial exposure to vacuum is incrementally increased at a rate producing a minimal moisture gradient from the inside of the root to its outside surface, thus preventing excessive pressure differentials. The same vacuum chamber is loaded with a titanium slug located at a distance sufficiently great from the tooth to preclude tooth surface splatter caused by the spitting titanium metal. Thereafter the titanium slug is exposed to an electron beam with the root exposed to the resulting vapor. To limit vapor deposition onto the tooth region which normally would be above the gums, that portion of the tooth is protected from the metal vapors by mechanical or lacquer masking. In this form the tooth may be mounted on the end of a rotating shaft so as to assure uniform vapor deposition. On completion, the excitation of the electron beam is shut off and the vacuum is released slowly to prevent diffusion and/or thermal shock. The titanium vapor deposited root is then reinserted into the vacant recess.

It has been found that a thin uniform (5000 angstrom or less) coating of titanium on the root promotes osseointegration to the patient's bone. Moreover, the concurrent exposure of the root to the vacuum and titanium vapor provides sterilization, thus minimizing the incidence of post-implant infection.

Accordingly teeth lost in the course of facial trauma, or extracted for repair, are conveniently re-implanted onto the subjacent bone. Such re-implantation is most successful if carried out within 24 to 48 hours after extraction, before the fibrous biological substance begin to fill the original cavity.

DESCRIPTION OF THE PREFERRED EMBODIMENT

Tooth loss as result of trauma or periodontal disease is an event of some frequency. Also frequent is the damage to the tooth root or tooth loss as a result of dental therapy (i.e. introgenic).

In each instance the supporting bone of the natural tooth is frequently viable and, if the titanium coated tooth is repositioned back into the void, the tooth has some chance for continued use. Nonetheless, a variety of natural processes often combine to preclude effective non-titanium coated tooth reimplantation. Most frequently, infection and growth of fibrous matter around the natural root do not allow reattachment of the tooth to bone with the result that such direct replacement methods are often less than successful.

In the past it has been found that titanium oxide (TiO2), exhibits molecular bonding processes with the living tissue that promote osseointegration. Thus, for example, the teachings of U.S Pat. No. 4,871,336 to Von Recum et al suggest deposition of titanium oxide onto soft polymeric patches to promote their implantation into living prostheses.

These advantages of titanium oxide combine synergistically with dehydration and sterilization of a tooth root in the titanium vapor deposition process disclosed herein.

Figure 1:
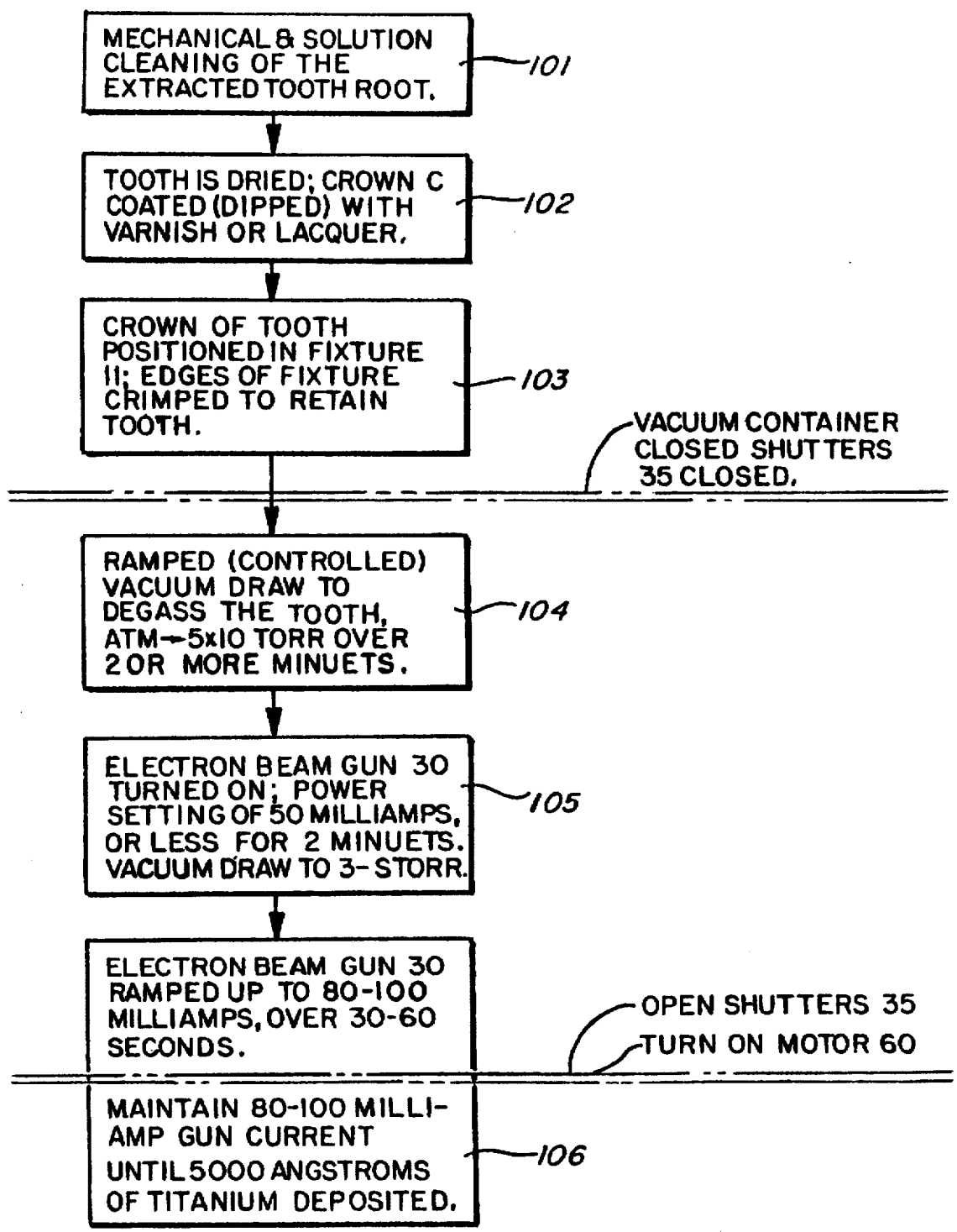
FIG. 1 is a sequence diagram illustrating the sequence of steps useful in carrying out the present inventive method.
Figure 2:
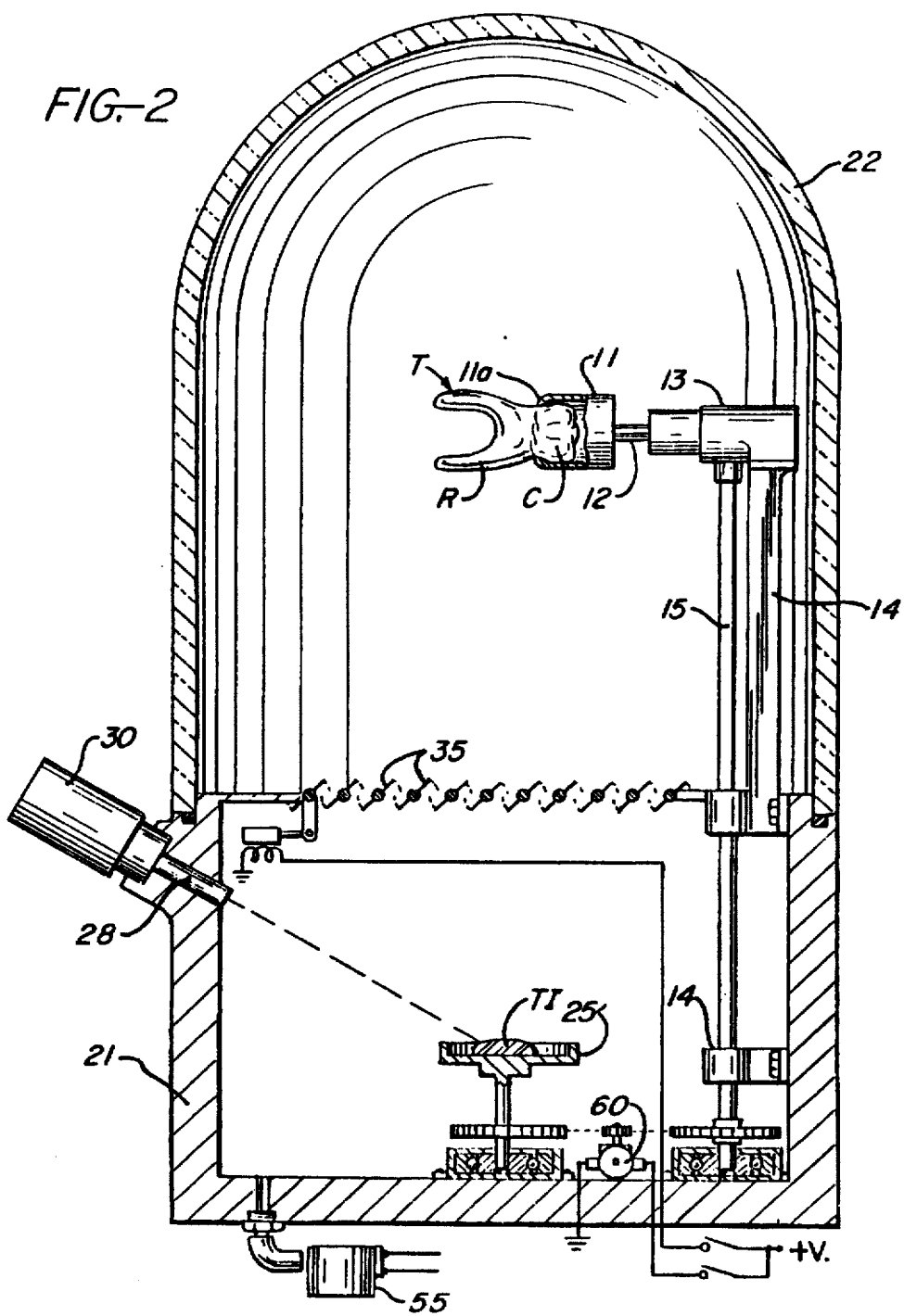
FIG. 2 is a diagrammatic illustration of the apparatus useful with the present invention.
Figure 3:
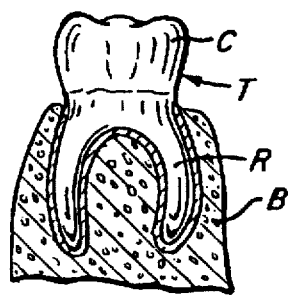
FIG. 3 is a sectional view of a tooth reimplanted onto a jaw bone in accordance with the present invention.

More precisely, by reference to FIGS. 1, 2 and 3, a tooth T is characterized by an enamel coated crown C and a depending root R which, in the course of growth, conforms to the local support shape of the bone B. Typically the structural compliance of the tooth T and the bone B are similar and, when properly fixed, sufficient force transfer is effected for mastication. Once, however, this tooth T is displaced from its natural position a variety of processes then combine to limit proper healing. Amongst these are the infection processes that follow any exposure of the root R.

In the process described herein the root R of the tooth T is first cleaned and the crown C is then received in a hollow masking fixture 11. This masking fixture 11 is mounted at the end of a rotary post 12 aligned for horizontal presentation of the exposed tooth root R.

A gear case 13 transfers rotary power to the horizontal post 12 from a vertical shaft 15 housed within a vertical tower 14. Tower 14, in turn, is supported at its base within the interior cavity of a housing shell 21, covered by a bell jar 22 which also encloses the tower assembly.

Deployed in spaced relationship directly below the cantilevered tooth root R, as it is fixed in the masking fixture 11, is a rotary hearth or dish 25 in which a slug of titanium TI is received. It is this titanium mass that is useful as the source of titanium vapor, according to the teachings below.

Preferably the spacing between dish 25 and the elevation of the cantilevered tooth T is such as to preclude any significant incidence of splatter, or metal spray, that may occur during the heating of the metal. Thus, a vertical spacing of 3 cm, or more, will effectively preclude such statistical events. An electron beam gun 30 proximate an inclined aperture or port 28 is then used to vaporize the titanium.

In the method described herein the tooth root R is first mechanically cleaned in a cleaning step 101 which may include various conventional cleaning and surface sterilization procedures like ultrasonic baths, autoclave and the like. Thereafter the tooth is dried externally and prepared for vapor deposition, in step 102, by coating the crown C with protective varnishes and the like. Once the extracted tooth is thus prepared its crown may be then inserted into the recess formed in fixture 11 and may be retained therein by crimping or bending the recess edges 11a, this positioning and retention sequence being shown as the positioning step 103. In the course of this step the tooth root R is exposed and aligned by line of sight exposure, to any vapors that may be emitted from the titanium slug.

The above subsequence of steps is generally manual in nature and includes events which are essentially unconstrained in the amounts of heat applied, vacuum drawn, or the rates thereof. Essentially each of the foregoing steps entails events or procedures which conform with standards of good practice such as those available in any dental office, including cleaning and sterilization sequences known in the art.

These preliminary steps are then followed by the closure of the containment cavity defined by the bell jar 22 and the lower housing shell 21. The enclosed, cleaned, protected, and now positioned tooth root R is then exposed to an increasing (ramped) vacuum draw, drawn by a vacuum pump 55 which is selected in its pumping rate to draw down a vacuum of $5 \times 10$ Torr, or less, over a time interval of 2 minutes or more. This gradual draw down rate is selected to allow the interstitial cavities within the root structure to degass without undue cracking or structural consequence. The controlled degassing draw down, shown as step 104, may be accomplished while a set of horizontally aligned shutters 35 are closed.

Shutters 35 are positioned above the dish 25, and when open, provide kinetic impact surfaces against which the splatter that may be released in the course of vaporizing the titanium impinges.

These same shutters are maintained in their closed position in the next step of the process, specifically step 105. In the course of this step the internal vacuum within the enclosure is maintained at a $5 \times 10$ Torr, or less, level while the electron beam gun 30 is turned to its initial, degassing, current level of 50 milliamps or less. This low current level is useful in pre-heating and degassing the titanium slug and a heating period of 1 to 2 minutes at this power setting is sufficient to stabilize the titanium slug.

Thereafter in step 106 the electron beam gun 30 is ramped up to 80–100 milliamperes, at 10 KVDC, over a period of 30–60 seconds, to fully degass the titanium. Following this interval the shutters 35 are then opened and the tooth root is then exposed to the titanium vapor. Of course, an electric motor 60, or other source of motive power, may be utilized to advance to mounted tooth in rotation and also to drive the disk 25. In this manner vapor deposition of titanium is maintained until a thickness of about 5000 angstroms is deposited on the root.

In this manner a substantially pure, uniform coating is applied to the tooth root which is first exposed to a vacuum. The combination of the vacuum and the surface temperature of the vapor coating combine for full root sterilization.

Obviously many modifications and changes may be made to the foregoing description without departing from the spirit of the invention. It is therefore intended that the scope of the invention be determined solely on the claims appended hereto.

What is claimed is:

1. A method for sterilizing and re-implanting a natural tooth including a crown and a root comprising the steps of:

masking the crown of said tooth;

mounting said tooth in one partitioned part of a vacuum container, the partition of said part capable of being selectively opened, said container further comprising another part which is separated from said part by said partition;

drawing a progressively increasing vacuum in said container at a rate sufficient to promote dehydration and degassing of the root of said tooth;

heating a mass of titanium in said another part of said container by applying progressively increasing beam energy at an increasing rate sufficient to promote outgassing;

opening the partition between said one part and said another part of said container upon the vaporization of a portion of said titanium mass; and removing said tooth from said container for the re-implantation thereof.

2. A method according to claim 1 wherein:

said step of opening of said partition is maintained until titanium vapor is collected on said root to a thickness greater than 5,000 angstroms.

3. A method according to claim 1 wherein:

said step of progressively drawing said vacuum is continued until a vacuum of $5 \times 10^3$ Torr, or less is drawn.

4. A method according to claim 3 wherein:

said step of progressively drawing said vacuum is maintained for a period greater than two minutes.

5. Apparatus for sterilizing a tooth root and vapor depositing titanium on the exterior thereof comprising:

a vacuum chamber including a first portion and a second portion;

separating means between said first and second portions selectively moveable to form a communication path therebetween;

a first mounting fixture formed in said first portion and having means for engaging said tooth therein;

a second mounting fixture formed in said second portion for supporting a mass of titanium metal therein, said first and second mounting fixtures being conformed for rotary articulation;

beam producing means connected to said chamber for directing an energy beam to said second mounting fixture;

vacuum pump means connected to said chamber for the evacuation thereof; and gearing means are connected between said first and second mounting fixtures for coordinating the rotary articulation thereof.

6. Apparatus according to claim 5 wherein:

said first and second mounting fixtures are conformed for rotary articulation; and gearing means connected between said first and second mounting fixtures for coordinating the rotary articulation thereof.

7. Apparatus according to claim 5 further comprising:

first control means connected to said beam producing means for controlling the energy thereof; and second control means connected to said vacuum pump means for controlling the rate thereof.

8. A method for treating a natural tooth after extraction comprising the steps of:

cleaning such tooth;

masking the crown of the tooth by mechanical means, and mounting said tooth in an evaporator on the end of a rotating rod in 90 degree position to a titanium vapor source;

gradually applying vacuum to slowly degas and dehydrate the tooth;

applying power to a beam generator for a length sufficient to vaporize titanium;

exposing the tooth to ambient surroundings; and re-inserting the tooth in the original cavity within 24 to 48 hours after original extraction.

* * * * *